United States Patent [19]
Bunce et al.

[11] Patent Number: 5,354,538
[45] Date of Patent: Oct. 11, 1994

[54] LIQUID TRANSFER DEVICES

[76] Inventors: Roger A. Bunce, Bournville; Gary H. G. H. Thorpe, Handsworth; John E. C. Gibbons, Hall Green; Louise J. Keen, Balsall Heath; Matthew R. Walker, Selly Oak, all of England

[*] Notice: The portion of the term of this patent subsequent to Mar. 30, 2010, has been disclaimed.

[21] Appl. No.: 961,542

[22] Filed: Oct. 15, 1992

Related U.S. Application Data

[63] Continuation of Ser. No. 601,697, Oct. 29, 1990, Pat. No. 5,198,193.

[30] Foreign Application Priority Data

Mar. 23, 1989 [GB] United Kingdom ............... 8906833
Oct. 6, 1989 [GB] United Kingdom ............... 8922513

[51] Int. Cl.⁵ .................................................. G01N 30/00
[52] U.S. Cl. ......................................... 422/100; 422/103; 422/58; 436/170; 436/169
[58] Field of Search ....................................... 422/56-58, 422/61, 73, 69, 100-103; 436/169, 170

[56] References Cited

FOREIGN PATENT DOCUMENTS 0212314 3/1987 European Pat. Off. .
0239174 9/1987 European Pat. Off. .
0262328 4/1988 European Pat. Off. .
WO88/07666 10/1988 PCT Int'l Appl. .
WO89/03992 5/1989 PCT Int'l Appl. .

*Primary Examiner*—James C. Rousel
*Assistant Examiner*—Rachel Freed
*Attorney, Agent, or Firm*—Nixon & Vanderhye

[57] ABSTRACT

A liquid transfer device of disposable one-time use form to conduct a biochemical diagnostic or other assay comprises two liquid flow channels (10,110,210; 20,120,220) leading from a respective pair of channel ends to a common site (30,130,230) and operable to deliver liquid to this site in sequentially timed manner following simultaneous application of such liquid to the channel ends. Typically respectively different reagents (11,111,211; 21,121,221) are incorporated in the two channels, and a third reagent (31,131,231) at the common site, whereby a sample to be assayed in respect of a particular content can be applied to the site, immobilized by the third reagent, subsequently subjected to one channel reagent to detect any of the content of interest, and finally subjected to the other channel reagent to exhibit for the user any detected content.

12 Claims, 13 Drawing Sheets

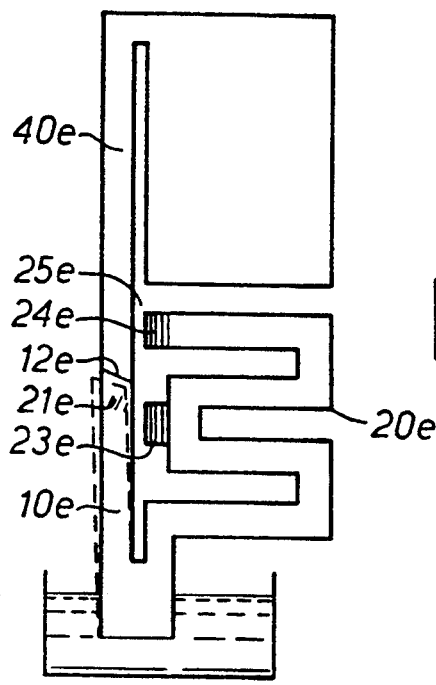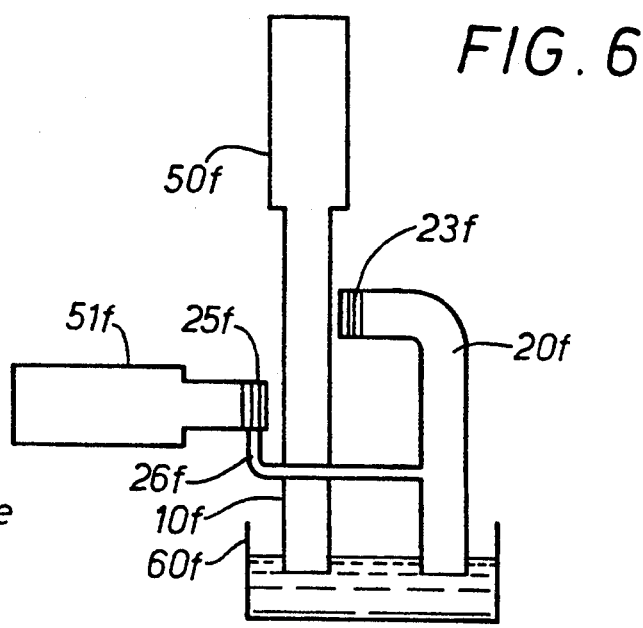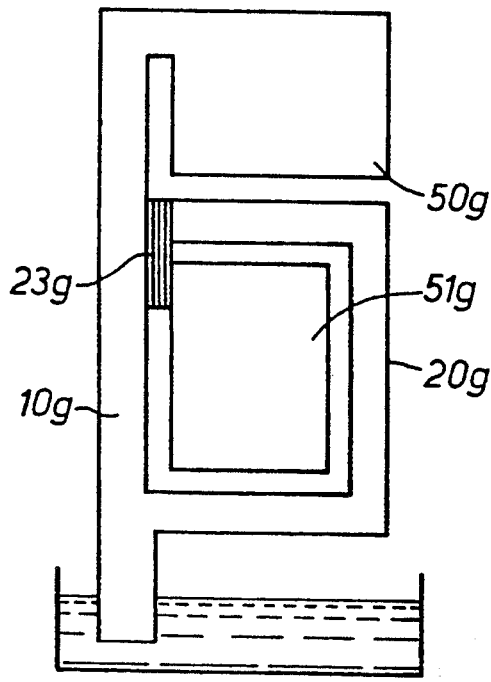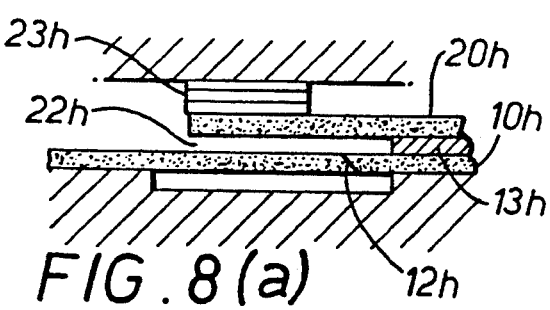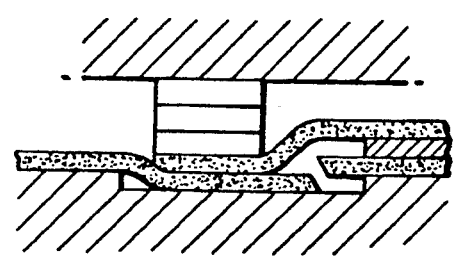

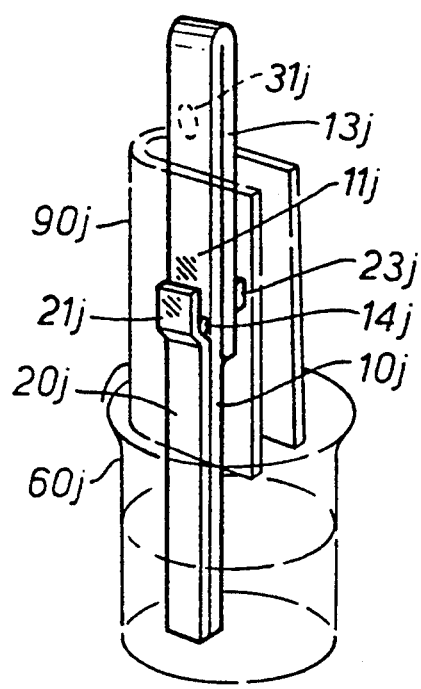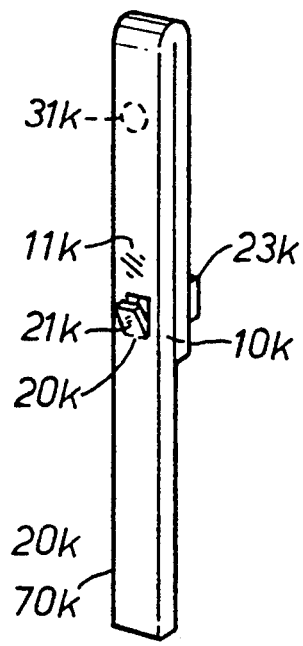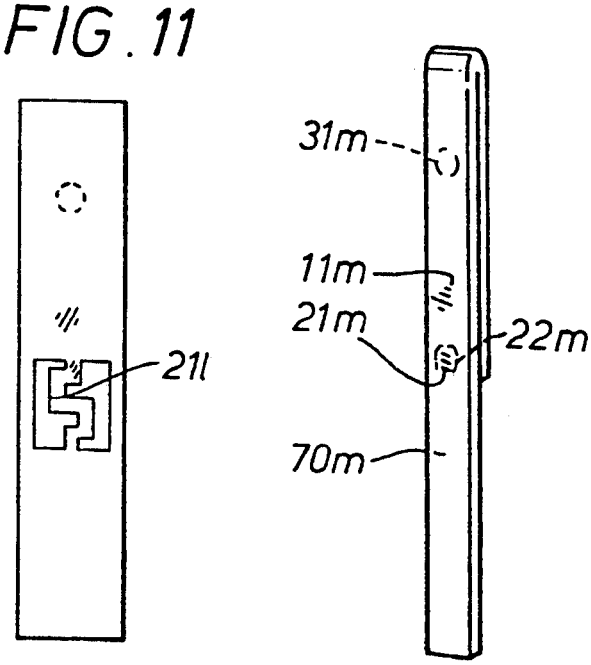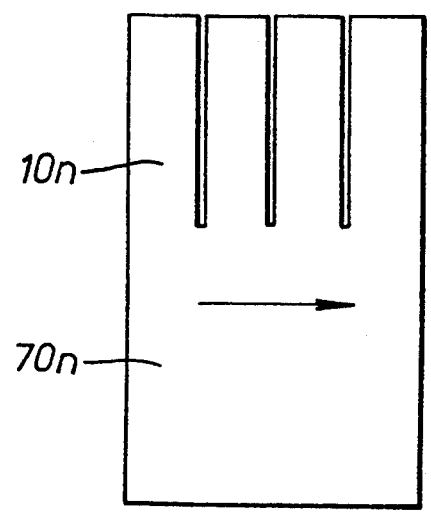

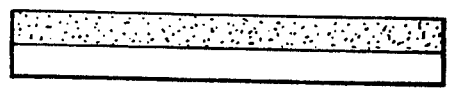
FIG. 24(a)    FIG. 24(b)
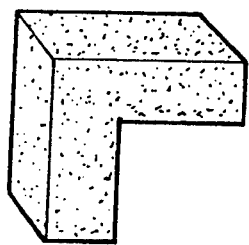
FIG. 25(a)    FIG. 25(b)
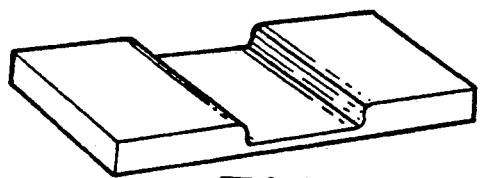
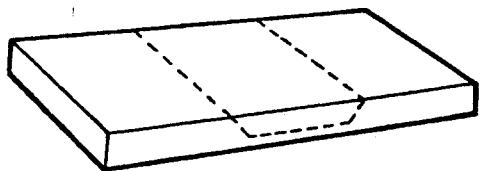
FIG. 26(a)    FIG. 26(b)

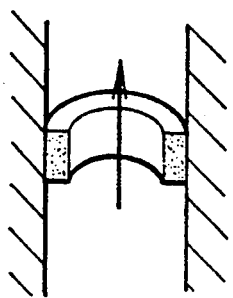
FIG. 36(a)
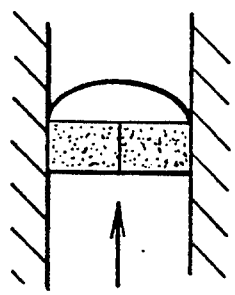
FIG. 36(b)
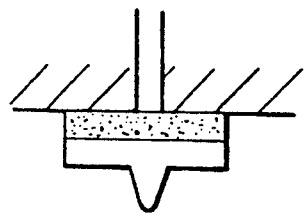
FIG. 37(a)
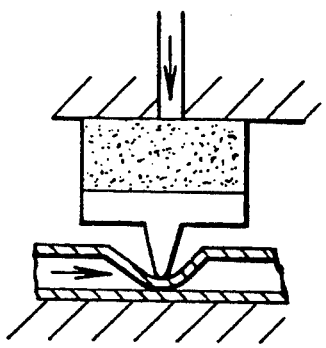
FIG. 37(b)
FIG. 39
FIG. 41
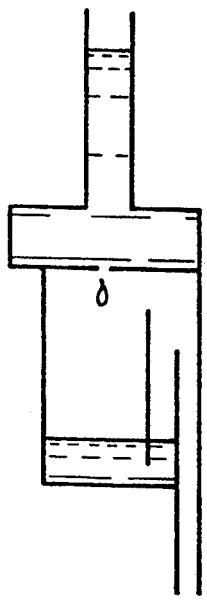
FIG. 38
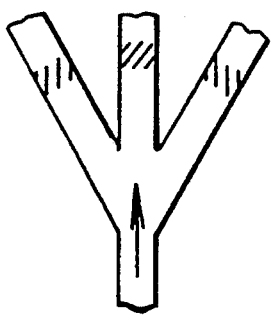
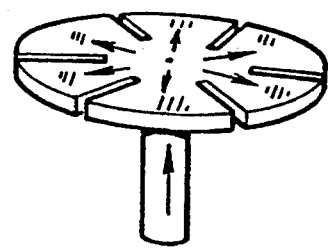
FIG. 40

LIQUID TRANSFER DEVICES

This is a continuation of application Ser. No. 07/601,697, filed Oct. 29, 1990, now U.S. Pat. No. 5,198,193.

BACKGROUND OF THE INVENTION

There is considerable commercial interest in simple analytical devices, usually of disposable, one-time use form, intended for extra-laboratory usage to conduct biochemical diagnostic assays. Ideally such devices should be operable in a satisfactory manner by lay persons, but this is not as yet normally the case in practice. Many of the currently available devices in fact involve complex manual procedures, with a common feature of such procedures being a requirement to effect a timed sequence of reagent additions to an analyte.

SUMMARY OF THE INVENTION

An object of the present invention is to improve this situation and, to this end, there is provided a liquid transfer device comprising two channels leading from a pair of respective channel ends to a common site and operable to deliver liquid to said site in sequentially timed manner following simultaneous application of such liquid to said channel ends.

In application to an analytical device, the site to which liquid is to be delivered will typically be one at which analysis is to be effected following deposition there of a sample to be tested in respect of an analyte of interest. Correspondingly the liquid to be delivered by each channel will typically comprise an individual reagent or a diluent, with the relevant channel usually bearing a reagent to be entrained by diluent flow In the latter case. The reagent and/or diluent for delivery can emanate from one or more reservoirs associated with or incorporated in the device. Similarly the device can be associated with or incorporate one or more reservoirs for the purposes of drainage of waste liquid.

The proposed device will, of course, involve liquid flow along its channels and this can involve two basically different forms of flow. One such form Is that resulting from predominantly capillary action and this will normally involve the use of porous material to define a related channel. Alternatively, capillary flow can involve channel definition by impermeable material in tubular, canal and other formations. The other form of flow is that resulting from predominantly gravitational or pressure forces and this is referred to hereinafter where appropriate as non-capillary flow. Non-capillary flow will normally involve channels defined by impermeable material in tubular, canal and other formations but, alternatively, can involve porous material. In both cases the impermeable material and porous material can be combined to form channels. Also, the two forms of flow are not mutually exclusively applicable to a given channel but can, if desired, be deployed in successive longitudinal portions of the same channel.

Operation of the proposed device to deliver liquid in sequentially timed manner inherently involves delay of the liquid flow along one channel relative to the other and various mechanisms are contemplated for this purpose. These mechanisms fall into two basic categories respectively involving differential flow path lengths and flow rates, and mechanisms of each category are applicable to each form of liquid flow. For example, the transit time of a capillary liquid flow along a path will clearly vary with path length when the path is that of a porous material channel of given uniform cross section, and the same is true for a non-capillary flow along a path extending upwardly through a hollow formation of similarly uniform cross section to be filled by the flow before continuance of the latter. Correspondingly the rates of such flows can be differentiated by variation of the cross sections of the respective channels.

A preferred form of flow rate delay mechanism for use in connection with capillary flow involves the provision of one channel of porous material in a compacted form expansible upon hydration to bridge, directly or indirectly, a subsequent gap in such channel.

As with the liquid flow forms, these delay mechanisms and their categories are not exclusively applicable to a single channel.

In addition to the delivery at a common site of liquids in sequentially timed manner, it may be appropriate that the relatively non-delayed flow at the site be terminated prior to on-site delivery of the delayed flow, and the present invention also contemplates the provision of mechanisms for this purpose. Different forms of such switch mechanisms can be provided for use in connection with different forms of liquid flow.

A preferred form of such a switch mechanism for use in connection with capillary flow involves the provision in one channel of porous material in a compacted form expansible upon hydration to open a gap in another channel.

As will be seen from the following more detailed description of the invention by way of example, it will typically be the case that the channels of the device merge into a common structure, in order that both shall access the common site, say. This is particularly the case when the device involves capillary flow in a porous material. Similarly, merging can effectively occur between successive portions of a single channel, such as when an expansible element forms a connection. In any event, development of the invention has shown it to be preferable that any such merging be effected in a substantially symmetrical manner relative to the on-going flow channel, at least from a hydraulic point of view, otherwise a non-uniform flow can occur with consequent unreliability or inconsistency of operation. Clearly symmetrical merging can be attained when one channel joins another wholly across the width of the latter in alignment with the on-going flow direction. However, it can be appropriate to merge one channel into a central portion, or similar opposite side portions, of another channel for this purpose. It can, in any case, be beneficial to taper or otherwise narrow the downstream end portion of the one channel to be centrally merged with another channel as this concentrates the merged flow along the desired path.

Lastly, in this more general consideration of the invention and various forms thereof, it will be appreciated that, while reference has been made to two channels and a single common site, compound devices having an increased number of channels and/or more than one site can be provided to accommodate more complex analytical operations.

BRIEF DESCRIPTION OF THE DRAWINGS

In any event, fuller understanding of the invention and its forms may be gained by consideration of specific embodiments thereof which are given by way of example and described below with reference to the accompanying drawings in which:

FIGS. 2-14 similarly illustrate generally progressive modifications of the embodiment of FIG. 1;

FIGS. 19-41 illustrate modifications in detail variously applicable to these embodiments.

DETAILED DESCRIPTION OF THE INVENTION

In describing the illustrated embodiments it is assumed that analysis is to be conducted in respect of an analyte in the form of antigen within a body fluid such as blood or urine of which a sample is made available. It is further assumed that the antigen will first be specifically bound with antibody held at the analysis site, then labelled by a first reagent, and finally subjected to a label detection second reagent to make a colorimetric or other output available. Such an analytical procedure is appropriate to a wide range of analytes of diagnostic interest and so represents a practical basis for exemplifying utilization of the embodiments. It will be appreciated however that the specific device embodiments and, indeed, other devices according to the invention are not intended to be limited to adaptation and use for such a procedure.

Figure 1:
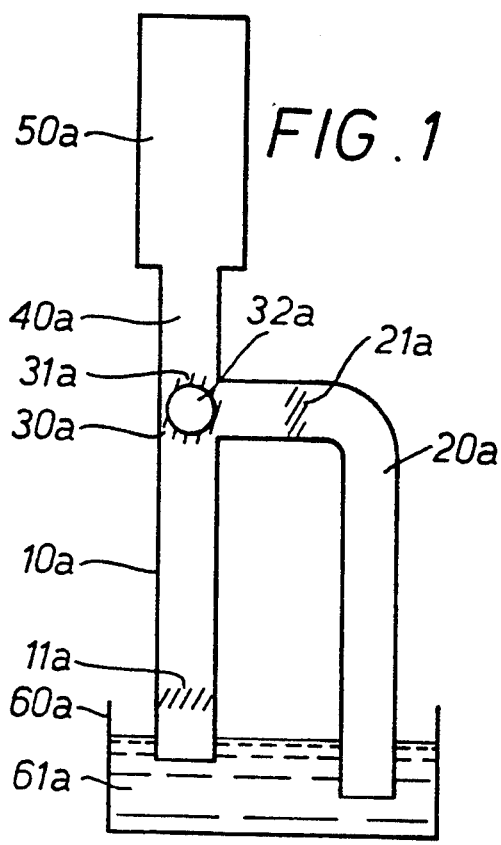
FIG. 1 schematically illustrates one embodiment of a device according to the invention involving capillary flow.

In any event the embodiment of FIG. 1 involves capillary flow through porous material such as of filter paper type. There are first and second channels 10a and 20a of like uniform cross section but relatively shorter and longer lengths extending from respective individual free ends to a junction 30a. A third channel 40a extends from the junction to an area 50a of enlarged cross section. This porous material structure is shown as though located in a common vertical plane with the channels 10a and 20a depending to different extents downwardly into a liquid reservoir vessel 60a. In fact other dispositions are equally practicable, with a generally horizontal one being beneficial in minimising gravitational effects on the liquid flow, provided that the free end regions of the channels extend differentially into the vessel as shown.

The device is completed for carrying out the above analytical procedure by immobilisation of specific antibodies within a zone 31a of the porous material at junction 30a to serve as the analysis site, a surface of such zone being overlaid with a serum separation layer 32a. Also, first and second reagents are impregnated into respective zones 11a and 21a of the channels 10a and 20a.

In use of the device the vessel 60a is charged with diluent 61a, a sample for analysis is applied to the layer 32a, and the free ends of the channels are immersed in the diluent as shown. Antigen of interest migrates to the zone 31a and is bound by the antibodies, while diluent flows up the channels 10a and 20a to solubilise and entrain the reagents at zones 11a and 21a to carry the latter onwards to the zone 31a. In operation the channel flows will of course take time to reach zone 31a; the times for such flows will differ by virtue of the different channel lengths with channel 10a being shorter and therefore faster than 20a; and the diluent vessel volume, the channel material absorbancies and the channel dependencies into the vessel are such that the diluent level in the vessel falls below channel 10a after the flow in such channel has reached zone 31a and before the flow in channel 20a has reached zone 31a.

In the result, initiation of operation substantially predetermines a period for serum/immobilised antibody incubation at zone 31a, this period being terminated by arrival of the flow in channel 10a to label the antibody-bound antigen and flush unbound serum content onwardly through channel 40a to area 50a which serves as a waste reservoir, and following a further substantially predetermined incubation period the flow in channel 10a terminates while that in channel 20a arrives at zone 31a to detect the bound label and flush other constituents to the waste reservoir.

This embodiment will be seen to demonstrate a delay mechanism dependent on variation of channel lengths and also a switch mechanism deploying variation of channel/reservoir interconnection to terminate one flow before another is effective at an analysis site.

Also, it will be seen that flow from channel 10a can partially divert to channel 20a and this may cause an undesirable reagent reaction at zone 21a. Such an event is obviated by the modified embodiment of FIG. 2.

Figure 2:
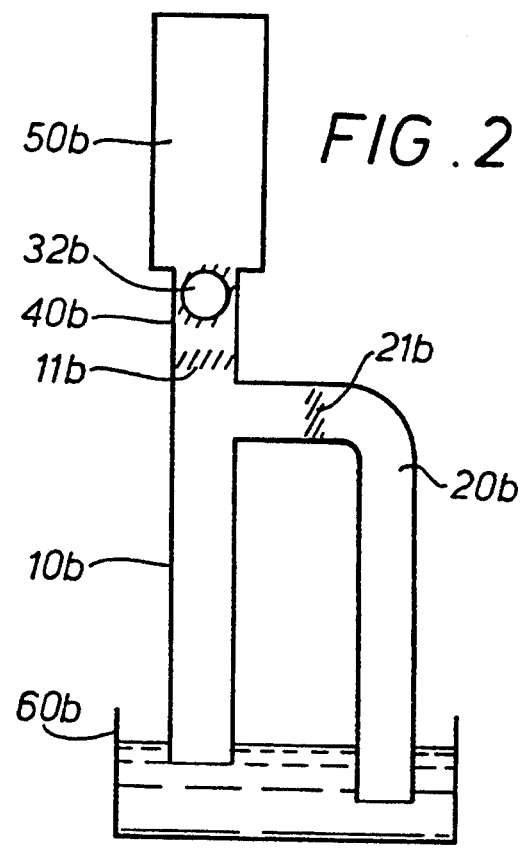

FIG. 2 is largely the same as that of FIG. 1 and so the same reference numerals are deployed for corresponding integers, but with the 'a' changed to 'b'.

The difference of FIG. 2 from FIG. 1 is in fact relatively simple and involves relocation of the first reagent and analysis site zones 11b and 31b in the third channel 40b.

Figure 3:
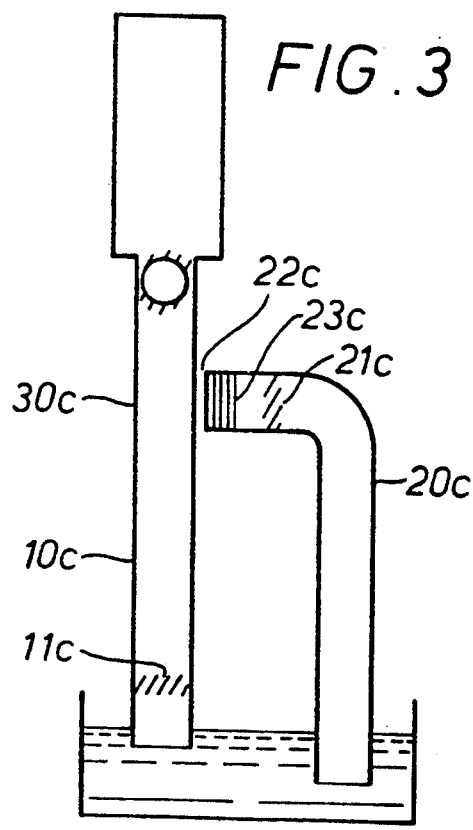

FIG. 3 shows an alternative to FIG. 2, again with use of the same reference numerals for corresponding integers but with the addition of a 'c' for purposes of distinction.

The different approach in FIG. 3 involves the provision of a gap 22c between channel 20c and the junction 30c while terminating the adjacent end of such channel in a compressed or otherwise compacted zone 23c, which last zone is expansible when hydrated to close the gap effectively by a switch action. In this case liquid flow in channel 10c cannot divert into channel 20c until the gap 22c becomes closed, at which time, appropriately, flow in channel 10c has terminated. It is to be noted that this feature can also serve as a delay mechanism.

In development of the Invention to date use of material other than of filter paper type, such as PVA cellulose foam, has been found appropriate for consistency of expansion action.

The common switch mechanism of FIGS. 1-3 may not be fully satisfactory for practical purposes in that the timing of its operation depends on the depth of channel immersion in diluent and this will vary with the extent to which the diluent reservoir is charged. This situation is avoided by the modified embodiment of FIG. 4.

Again, it is convenient to carry over reference numerals for corresponding integers but with distinction by 'd'.

Figure 4:
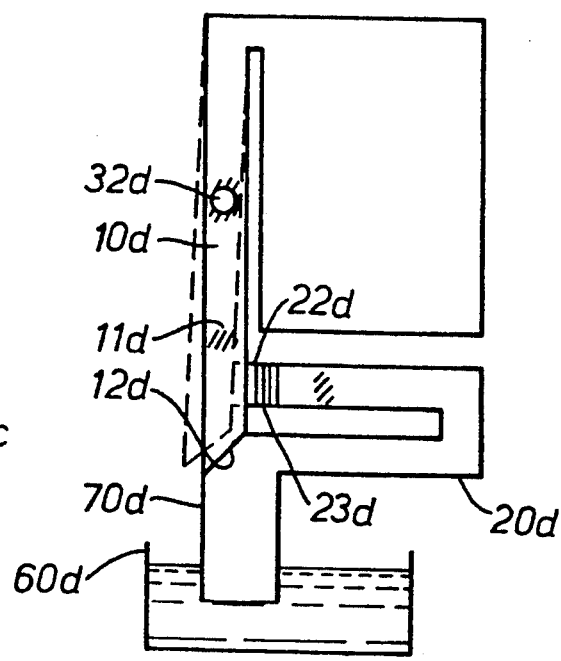

A first modification in the embodiment of FIG. 4 is that the first and second channels 10d and 20d are joined in a common channel portion 70d leading to the diluent reservoir 60d.

A second modification is that the first channel 10d is transversely cut through at 12d at a position between its junction with portion 70d and its periphery bordering gap 22d.

A third modification is that the portion of channel 10d extending towards the analysis site from its cut 12d is transversely movable from an initial position in which its cut ends are mutually engaged.

Operation in this case is such that diluent flows through the first channel 10d to carry entrained first reagent to the analysis site 32d, and also in delayed manner through the second channel to entrain second reagent. When this second flow causes expansion of zone 23d to close gap 22d not only does the flow continue to the analysis site, but the first channel is also caused to move to separate its cut ends and terminate the flow therethrough.

This last embodiment and its operation will be seen to demonstrate an alternative switch mechanism which alternative involves a compacted zone of porous material expansible when hydrated to disconnect a channel. However, while this mechanism acts to disconnect flow to the analytical site through the first channel, it does not act to terminate liquid flow through the site altogether because the disconnection itself involves a new connection affording onward flow through the second channel to the site.

FIG. 5, using the same pattern of reference numeral progression, shows a yet further modification whereby liquid flow at the analysis site is terminated for a period between first and second reagent delivery.

In this case the expansible compacted zone 23e moves the portion of channel 10e extending from its cut 12e towards the diluent reservoir, while channel 20e continues from its zone 23e towards another such zone 24e separated from channel 40e by another gap 25e, and the second reagent zone 21e is resited to a position between the compacted zones 23e and 24e. With this arrangement the first channel is disconnected and liquid flow to the analysis site is terminated wholly until after the second channel is connected.

FIG. 6 shows a further modification of an expansible mechanism to disconnect flow from one channel towards an analysis site when another channel is connected. In the arrangements already described this involves separation of successive lengths of the one channel which lengths initially interconnect by abutment rather than integration for the purposes of throughflow. A potential difficulty with such an abutment interconnection is that it is liable to disturbance by improper handling.

In FIG. 6 the one channel 10f is of integrated form and the other channel 20f connects by way of an expansible element 23f. Disconnection of flow wholly along channel 10f is effected by way of a further expansible element 25f activated by way of a branch channel 26f from channel 20f and connected, in turn, to a related waste reservoir 51f. Expansible element 25f connects with channel 10f upstream of element 23f.

Operation is such that, when both expansible elements are activated, flow will occur along channel 10f from reservoir 60f through element 25f and further along the channel while, at the same time, flow through element 23f from channel 20f will continue both up and down channel 10f. In the result the opposed flows in channel 10f between the elements produce a stagnant region, so that the initial flow in channel 10f from reservoir 60f is effectively disconnected by diversion to reservoir 51f.

FIG. 7 shows a modification of FIG. 6 in which the previously separate expansible elements are integrated at 23g in a coplanar channel arrangement.

FIG. 8 illustrates a modification in detail whereby the expansible mechanisms of FIGS. 3–7 are improved. In the embodiments of these earlier figures expansion occurs to join one channel into communication with the edge of another. The resulting flow in the other channel can tend, especially when this channel is already wet, to occur preferentially along the relevant edge so as to be non-uniformly distributed across the channel and give rise to a correspondingly non-uniform reaction.

In FIG. 8 the channels 10h and 20h, an impervious channel-separating layer 13h, and expansion element 23h are relatively superposed as shown at (a) to produce, when activated, a more extensive and complete communication as shown at (b). Given that the channels will typically be thin relative to their width, the resultant communication is substantially symmetrical from an hydraulic point of view.

Such modification is applicable simply to the making of a flow connection or, as in fact shown in FIG. 8(b), the simultaneous making of a connection and related disconnection. Also, an expansible mechanism can be used to move a related channel to solubilise and entrain into the channel a dry reagent located on an adjacent initially spaced surface.

FIG. 9 shows one embodiment of a device which employs this last modification to allow construction in a relatively compact so-called "dipstick" configuration comprising first and second channels 10j and 20j of porous strip material in generally superimposed relation. These channels are relatively longer and shorter and they are held together to extend from one pair of corresponding proximal ends along a rectilinear path over a major portion of the length of the shorter second channel. The first channel continues along this path for a distance, then turns to return over the same path, and terminates with its distal end short of the initial channel ends. The returning portion of the first channel is located remotely from the second channel and is held to the initial portion in association with an intervening liquid-impermeable barrier 13j. The distal end portion of the second channel bends away to a disposition spaced from the first channel where it is normally held by a relatively short length of separating material 14j.

A first reagent is impregnated in the first channel at a zone 11j located distally of the junction where the first channel and second channel distal end portion separate, a second reagent is impregnated in the second channel at a zone 21j located in the last-mentioned portion, and an analysis site is located in the first channel at zone 31j distally of the zone 11j.

The device also includes a switch mechanism involving a zone 23j of compacted porous material which is expansible when hydrated and located on the returning portion of the first channel opposite to the distal end portion of the second channel. This zone cooperates with a sleeve 90j, shown as a length of material having a generally U-shape cross-sectional form into which the channel structure can be slid.

In use of the device a sample to be analysed is applied to zone 31j and the proximal end portions are thereafter hydrated with diluent from a reservoir 60j shown as a beaker into which these portions are stood. Diluent then flows up the channels by capillary action towards the zones 11j and 21j to solubilise and entrain the respective reagents at these zones. The first reagent in fact is carried on in a continuous manner to the analysis site zone 31j with diluent and waste products passing on along the first channel. The second reagent, however, is carried to the distal end of the second channel where it stops pending further action. In this last connection appropriate further action occurs when the continuing diluent flow in the first channel passes down the returning portion of this channel to the site of the switch zone 23j which is then hydrated, with consequent expansion. This expansion initially engages the zone with the adjacent wall of the sleeve 90j and then, by reaction with the sleeve, pushes the adjoining part of the first channel towards engagement with the distal end portion of the second channel. This last engagement, in turn, allows solubilised second reagent to pass into the first channel and flow to the analysis zone, with waste products continuing on along the first channel.

It will be appreciated that, while it is appropriate in this last device to separate the 'rising' portion of the first channel from its continuing return portion with a liquid-impermeable barrier, no such measure is necessary between the former portion and the adjoining portion of the second channel. This appreciation has led to a further improved form of device as shown by FIG. 10.

In the device of FIG. 10 the first and second channels are, in effect, largely integrated into a single strip 70k, with the distal end portion of the second channel being formed by a tab 21k cut and bent out from this strip, while the adjacent remaining side arms and on-going portion of the strip serve as the first channel 10k. The overall sequence of events in use will be the same as for FIG. 9, with operation of the switch causing the tab and the initially-separate parts of the strip to move into engagement to allow continuing flow for the second reagent.

The advantage of this device lies in its simplified structure, and hence its production, compared to that of FIG. 9.

FIG. 11 shows a yet further improvement whereby the two channels are further integrated compared to FIG. 10, in a coplanar structure. In this case the distal end portion of the second channel 21l is not cut and bent out to form a tab, but instead is narrowed by strip material excision to form the same as a central arm spaced from the side arm portions of the first channel. The excision can be such as to provide a tortuous elongated longitudinal form for the second channel distal end portion compared to the straight first channel side arm portions, as shown, whereby through-flow in the former to carry the second reagent to the analysis site is delayed relative to that through the latter to carry the first reagent to the site. Alternatively, or in addition, the distal end of the central arm can be cut and longitudinally proximally compacted to form an expansible mechanism causing delay.

Other delay alternatives can involve the provision of a central arm area of greater cross sectional extent than the side arms to act like a slow-to-fill reservoir, a central area which is extended out of the plane of the side arms and then back again, or use of a slower wicking material for the central arm.

In the device of FIG. 12 the channels are still further structurally integrated in that the distal end portion 21m of the second channel is defined by an appropriately shaped impregnation of the strip with a soluble material to act as a temporary flow barrier 22m. This last material is to be such as to render the impregnated strip non-porous for the purposes of capillary flow therethrough when dry, but to solubilise upon hydration by the diluent and allow on-going flow with entrained second reagent after an interval appropriate for the sequencing purposes of the analytical procedure at hand. Materials so far considered useful for this purpose include lactose, starch and salt.

The advantage of the devices of FIGS. 11 and 12 clearly lies in their effectively solid state form which further facilitates manufacture and the provision of products more uniformly consistent in operation.

While the devices of FIGS. 9-12 are shown in singular form, they are amenable to provision in a plural form such as indicated by the configuration of FIG. 13. In FIG. 13 the proximal end portions of the respective device channels are integrated in the continuous area 70n, while the distal portions are separated into individual strips 10n by intervening slots. Such a configuration is suited to production by way of long lengths extending in the direction of the arrow in FIG. 13, with subdivision into discrete singular or plural device structures by cutting transversely to the arrow.

A plural form can offer various benefits including quality and/or standards testing in a procedure involving the same analyte, or parallel testing for different analytes, by way of a single device. Also, such a form can be used to quantify the amount of an analyte present by use of progressively varying strengths of reagents from one channel to the next to represent a calibrated scale.

Figure 14:
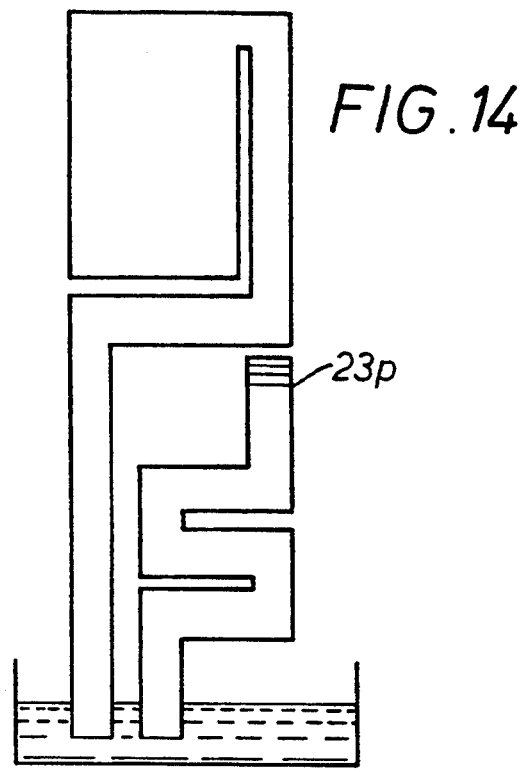

FIG. 14 shows an alternative modification for an improved expansible connection mechanism whereby undesirably non-uniform flow is avoided. In this case the two channels are coplanar, the first channel extends between proximal and distal portions through an angle, and the second channel has an expansible mechanism 23p operable to connect with the first channel distal portion in longitudinally aligned manner. In fact such an aligned connection configuration is beneficially applicable to devices such as those of FIGS. 1 and 2 where no expansible mechanism is involved.

Figure 15:
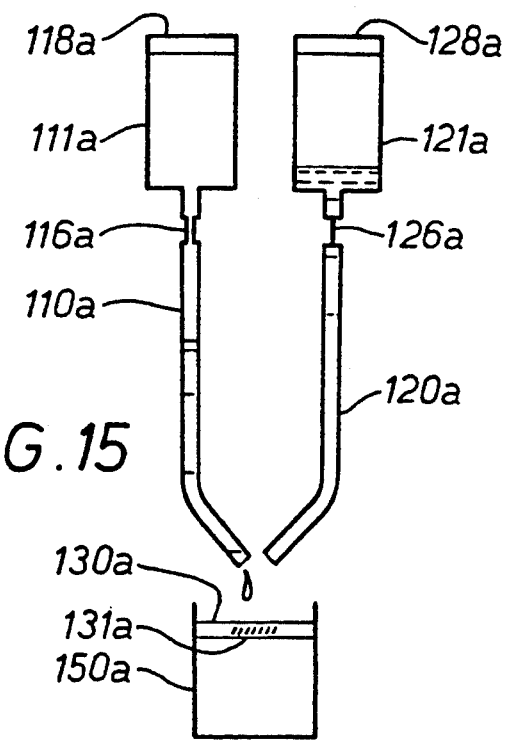
FIGS. 15 and 16 schematically illustrate embodiments involving non-capillary flow.

The embodiment of FIG. 15 involves non-capillary flow and follows, so far as is practicable, the convention established above for reference numerals but with the addition of a hundred digit for purposes of distinction.

The embodiment comprises first and second channels 110a and 120a defined by tubes depending above a waste reservoir vessel 150a having, extending across an upper region thereof, a member 130a of porous material. Specific antibodies are immobilised in a zone 131a of member 130a. At their upper ends the channels 110a and 120a are joined respectively through major and minor restrictions 116a and 126a to first and second reagent reservoir vessels 111a and 121a closed with hydrophobic vents 118a and 128a.

In use of this embodiment appropriate volumes of reagents are charged into vessels 111a and 121a and these vessels connected with their respective channels when inverted, sample is applied to member 130a, and the vessels and channels are located upright disposition over the member. The reagents flow from the vessels to their channels, but at differential rates by virtue of the intervening restrictors. The arrangement is to be such that channel 110a will contain the volume of first reagent whereby this volume is held in the channel and released rapidly only when it completes its flow through its restrictor, the subsequent air flow suffering negligible delay because of its far lesser viscosity. This allows a period for antigen/immobilised antibody incubation whereafter labelling and flushing occur. Similarly after a further incubation period the second reagent flows from its channel to detect the labelled matter.

Figure 16:
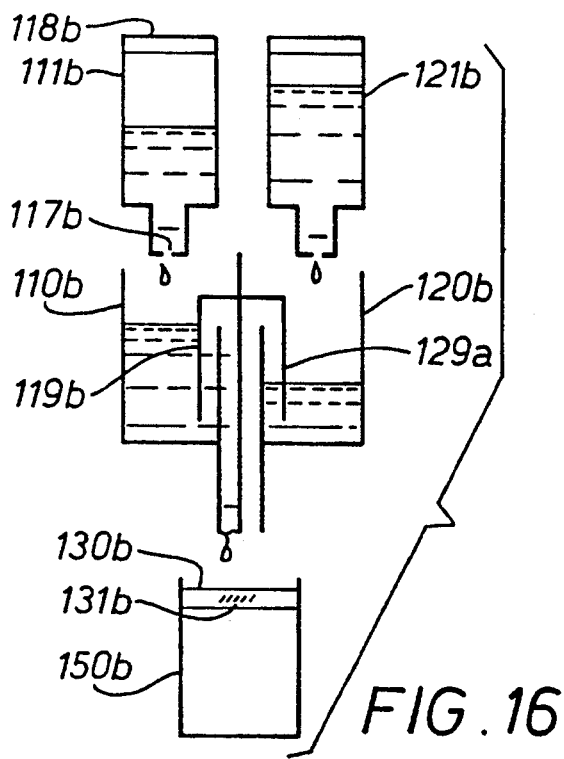

FIG. 16 illustrates a further embodiment involving non-capillary flow. The embodiment is similar to that of FIG. 10 but different restrictions and channels are employed.

In this case the restrictions are in the form of orifice outlets 117b and 127b from the vessels 111b and 121b, with these outlets being disposed, in use, above channels involving further vessels 110b and 120b having the inlet arms of siphons 119b and 129b depending therein in sealed manner from below the vessel rims. The siphon outlet arms are disposed above the porous member 130b.

Use and operation of this embodiment is similar to that of FIG. 10 but with the reagents flowing through their restrictions at different rates to initiate respective siphon flows following successive periods.

The embodiment of FIG. 16, of course, affords sequentially timed liquid delivery by way of differential flow rates through the restrictions. However, similar timing can be effected with like restrictions but siphon vessels of differing cross sectional area whereby filling to initiate siphon action takes different times in the two channels.

Figure 17:
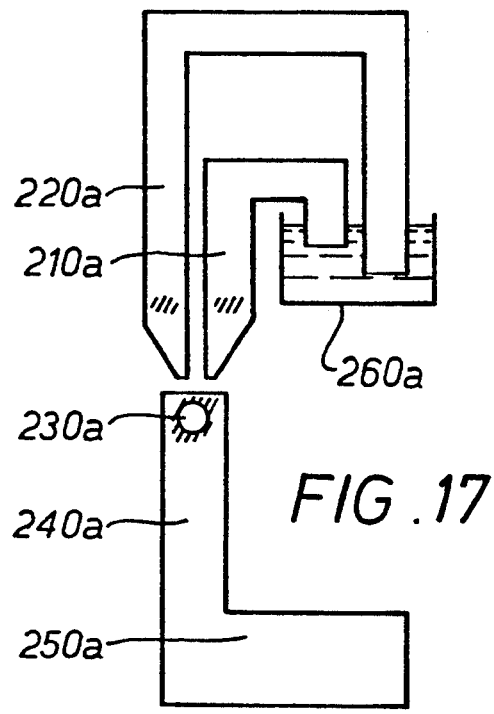
FIGS. 17 and 18 similarly illustrate respective embodiments each involving both capillary and non-capillary flow.

FIG. 17 shows an embodiment which is of hybrid form in that it involves both capillary and non-capillary flow. Again the same reference numerals as above are used for corresponding integers, but with the addition of a two hundreds digit.

In this embodiment channels 210a and 220a are of porous material, different lengths, and depend differentially into a common diluent reservoir 260a, similarly to the arrangements of FIGS. 1–3. However, the channels extend upwardly and then turn downwardly to terminate in tapered ends below the reservoir 260a to provide a siphon function in use. Liquid flowing through these channels drops from the tapered ends on to a third channel 240a of porous material spaced therebelow and flows on, through analysis site 230a in this channel, to a waste reservoir 250a.

Figure 18:
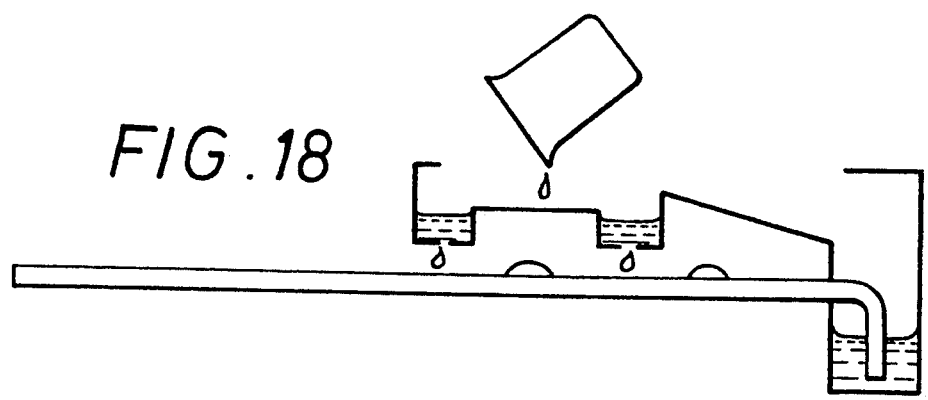

The embodiments described so far indicate the invention to be open to variation within the broader terms of the preceding introductory discussion and the scope for variation is emphasised, although not exhaustively indicated, by FIGS. 18– ... of the accompanying drawings.

FIG. 18 shows another hybrid embodiment using a single strip of porous material and a compound reservoir to which diluent is added directly to initiate operation following application of a sample to the analysis site. The reservoir has a proximal portion and two distal portions located respectively adjacent positions between the two reagent sites, on the one hand, and between the analysis site and the nearer reagent site, on the other hand. The resultant operation will wash the analysis site following sample addition, apply the nearer reagent to this site, wash the site again, apply the second reagent, and finally wash once again.

Figures 19, 20, 21:
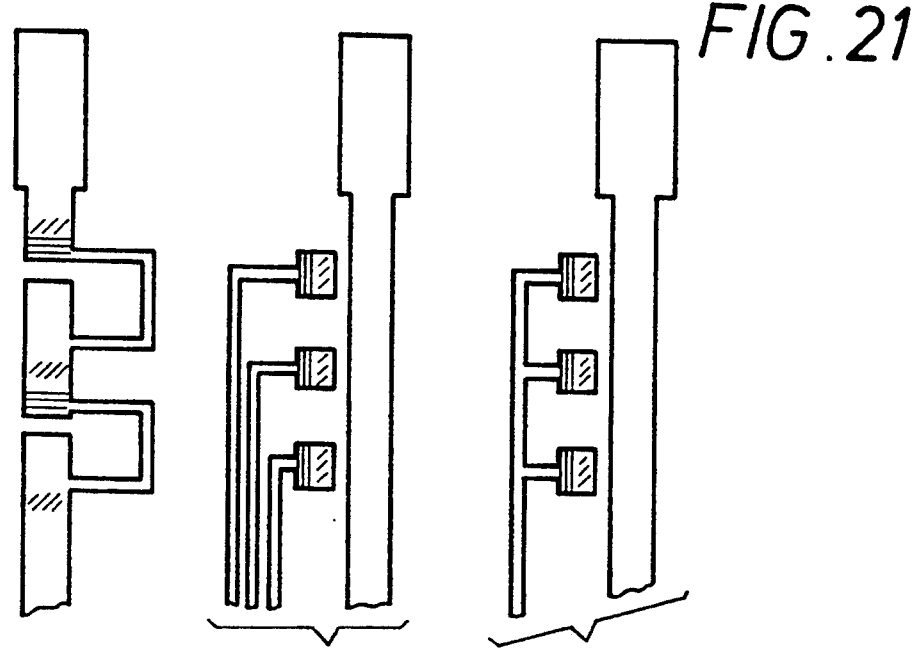

FIGS. 19–21 show respectively different arrangements whereby plural reagents can be added sequentially to flow in a common capillary channel. In FIG. 19 the channel itself is separated into successive segments which can each carry a reagent, and an expansible element with the latter each being activated by a respective subsidiary channel link to effect in-line connection with the preceding segment.

In FIG. 20 the channel is associated with a number of reagent-carrying expansible elements located adjacent successive regions along the channel length, the elements being successively activated by parallel subsidiary channels.

FIG. 21 is similar to FIG. 14 but with the subsidiary channels serially interconnected.

Figures 22, 23:
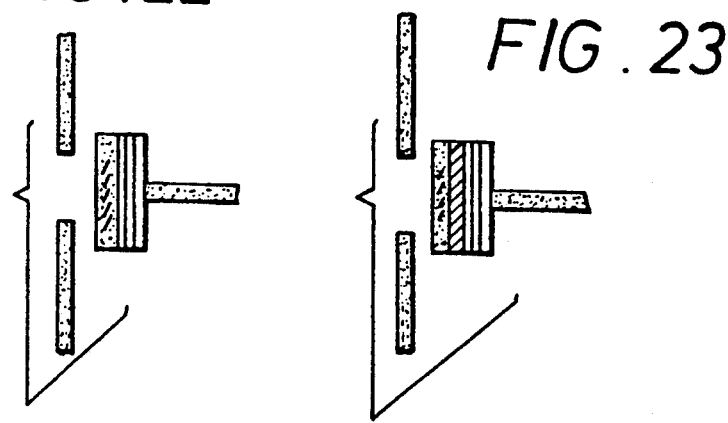

FIG. 22 shows reagent addition to a main channel by way of an expansible element activated by a subsidiary channel, with the subsidiary channel causing bridging of a gap in the main channel.

FIG. 23 is similar to FIG. 16 but includes an impervious membrane or layer located between the compacted and reagent-carrying zones of the expansible element.

FIG. 24 shows an alternative expansible element operable to effect channel connection or disconnection. In this case the element is made up of materials having respectively different hydration expansion properties, which materials form respective transversely-adjoining zones through the element. Operation will be like that of a bimetallic element, but with different geometrical configurations being assumed between dehydrated and hydrated conditions as at (a) and (b) for example.

FIG. 25 shows a further such alternative in which a porous material is compressed when dehydrated to an overall shape markedly different from that assumed when hydrated. For example, material having an L-shape when hydrated as at (a) can be compressed when dehydrated to a flattened slat-like shape as at (b), with rehydration causing a return to the L-shape.

FIG. 26 shows an expansible element formed by local compression between opposed areas of the major faces of a channel, with the element being indicated in its initial dry and then hydrated conditions respectively at (a) and (b).

Figure 27:
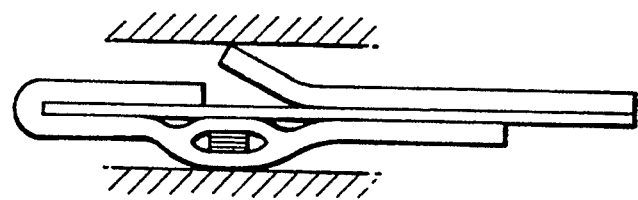
Figure 28:
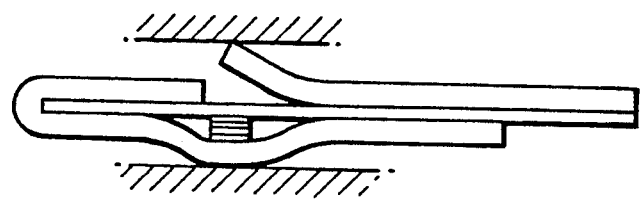

FIGS. 27 and 28 show expansible elements incorporated into a device in modified manner, In FIG. 27 the element is housed within the related hydrating channel itself, while in FIG. 28 the element is housed between the channel and an adjacent impervious layer.

It is in any case appropriate that an expansible element be securely engaged on or against its related channel, unless integrally formed therewith, to ensure that it is hydrated during operation of the device. A particular concern in this respect is that the formation of 'blisters' between the element and channel should be avoided otherwise separation can occur which is detrimental to reliable and consistent hydration. To this end engagement can suitably be effected by preloading, bearing in mind that the resultant engagement force should not be so low as still to allow blister formation, nor so high as to constrain the desired expansion. Alternatively, engagement is effected by glueing, in which case adhesive is applied in a distributed array of small areas of the relevant interface to act against blister formation while still allowing consistent hydration through the interface.

Figure 29:
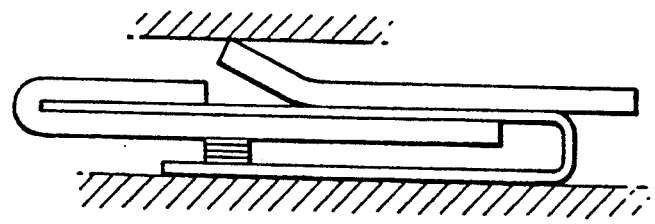

FIG. 29 illustrates preloading by use of a spring of plastics material, which spring additionally serves as an impervious channel separating layer.

Figure 30:
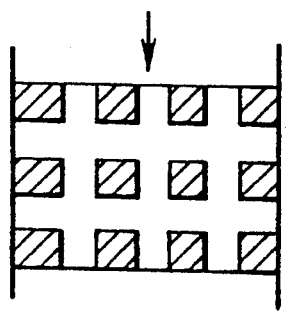
Figure 31:
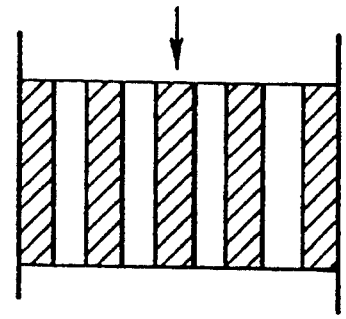

FIGS. 30 and 31 show respective examples of suitable glueing patterns.

Figure 32:
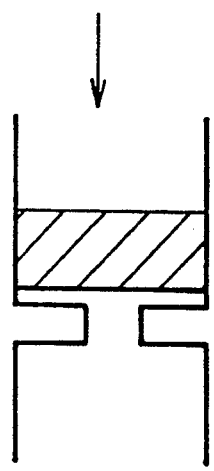
Figure 33:
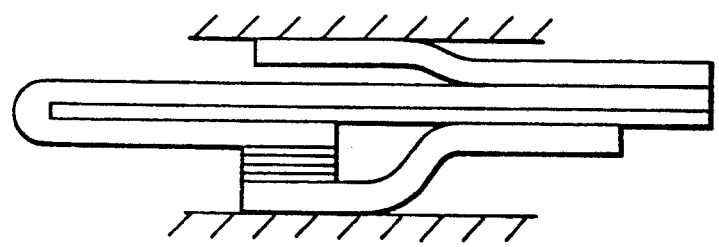

Another factor, which arises in devices such as those of FIGS. 9 and 10 in which an expansible element is fitted to a channel which continues beyond the element, is that the available liquid flow in the channel is apportioned between the element and on-going channel portion. In these circumstances expansion may be improved by the provision of a flow restriction In the channel adjacent the element as shown in FIG. 32. Alternatively liquid can be directed on through the channel by way of the element as shown in FIG. 33.

Figure 34:
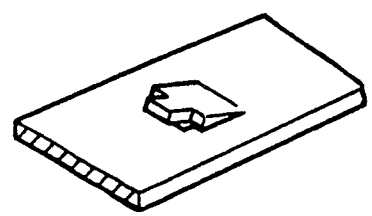

FIG. 34 shows an alternative form of tab for cooperation with an expansible element. In this case the tab is formed with shoulders which abut against the complementary formations in its parent channel to reduce any risk of premature closure other than by the related element.

In other alternatives, expansible elements can have a 3-dimensional form, rather than the effectively 2-dimensional forms indicated so far.

Figure 35A:
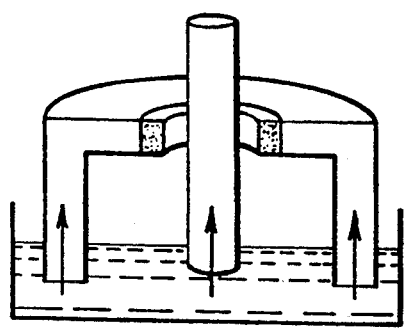
Figure 35B:
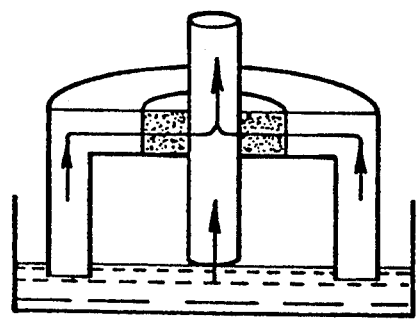

FIG. 35 illustrates one example involving an annular shaping, respectively dehydrated and hydrated at (a) and (b).

FIG. 36 shows another such example applicable, in this instance, to non-capillary flow to effect disconnection as indicated by the dehydrated and hydrated conditions at (a) and (b).

FIG. 37 similarly shows yet another example for disconnection of a non-capillary flow through a resilient tube.

It is appropriate to note in connection with expansible elements of the various forms indicated above that the porous material, such as PVA cellulose foam, will normally be of a resilient nature when hydrated. There is accordingly no necessity to provide closely matching shapes as between the element and a coating integer because the former will conform readily to the latter.

Flow connection and disconnection may also be effected chemically. For example a monomer in one channel and itself allowing flow in that channel may be converted to a polymer by an initiator from another channel, the polymer being such as to block the one channel. Conversely, one channel may include a polymeric blocking material dissolvable to allow throughflow by application of a solvent from another channel.

In another variation of flow controlling mechanisms use may be made of magnetism. For example, a reagent may be contained in or on magnetic material held at a particular location in a channel by an adjacent magnet or induced, when hydrated, to move towards such a location.

In a further variation applicable to porous material devices such as described above, the channel configurations can be defined by the application of an agent to render material in an intact sheet impervious in appropriate areas, as an alternative to excision or omission of those areas during device production.

Also it is to be noted that liquid flow along a transversely uniform channel of porous material is non-linear and it may be appropriate in some circumstances to provide a channel having, along its length, a progressively varying cross section to attain a relatively constant flow rate. This may be useful, for example, for a channel entry to a reservoir shortly preceded by an analysis or other such site so that a non-uniform flow does not cause an adverse upstream reaction at the site.

The embodiments and variations described so far have been related to an analytical procedure expressed in relatively simple fundamental terms. In practice such procedures may well be more complex in terms of the numbers of operational steps to be sequenced. For example, many such procedures involve the addition of two or more aliquots of wash solution following one reaction before another reaction is effected. Such a multiplication of steps is, of course, possible in use of the invention simply by an appropriate multiplication of channels and/or other elements. However, this might be seen as an undue complication in the case of non-capillary flow embodiments.

Resolution of this last situation can, for a successive wash requirement, for example, be met by a siphon arrangement such as that of FIG. 16 but with an increased reservoir capacity. Overall operation in this event will be such that the channel 110$b$, say, will fill to the level at which its siphon 119$b$ operates, this operation will be such as to empty the channel rapidly, and the channel will thereafter refill and operate again after an interval. However, when a siphon-supplying reservoir of essentially uniform cross-section is used, there is a limit to the ratio between the interval and the initial time leading up to the first siphon operation. This limiting ratio is about 2.4 whereas a value of at least about 3 is normal in conventionally effected procedures.

FIG. 38 shows a modified arrangement in which the siphon reservoir is of a stepped form having a narrowed upper portion. This allows ratios of up to about 6 to be achieved.

Also in application of the invention it will be useful in some circumstances if multiple analyses can be conducted in relation to one sample, such as when testing for allergies, for example.

FIG. 39 shows an embodiment detail for this purpose in which a sample-carrying channel divides into plural downstream channels in a forked or fanned array which can carry different primary reagents.

FIG. 40 shows another such embodiment detail in which the channel divides radially into a plural discform array.

FIG. 41 shows yet another such embodiment detail in which a main channel is separated over part of its length into plural subsidiary channels carrying respectively different immobilised reagents, for example.

The remaining FIGS. 42–45 of the drawings illustrate specific devices employed in experiments serving to demonstrate the practical viability of the invention for routine usage.

Figure 42:
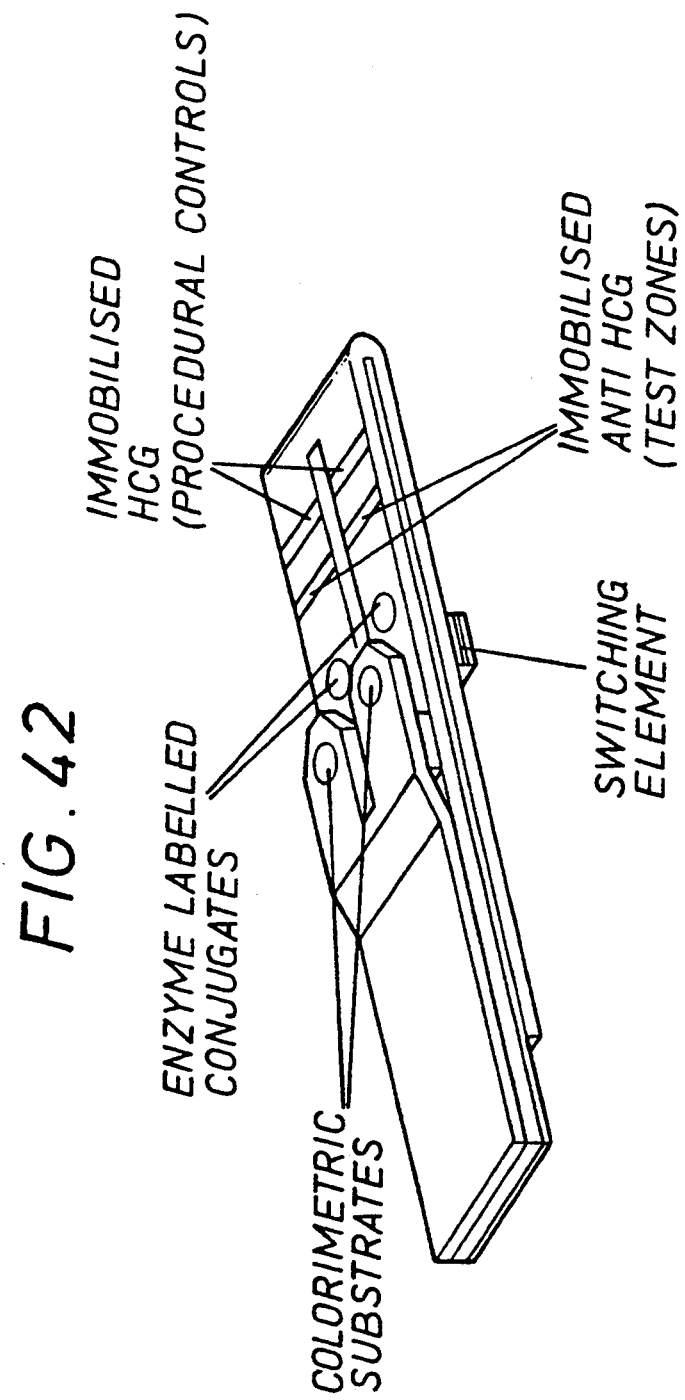
FIGS. 42-45 illustrate respective specific embodiments described in relation to experimental usage for assay procedures.

The device of FIG. 42 has a superficial size of 92 × 14 mm and is proportioned in its detail essentially as illustrated. Also, it will be seen that the device is of twinned partially integrated form although, for convenience, described below in the singular. The twinned form allowed simultaneous testing of two samples.

The main channel and switch channel of the device were cut from Whatman glass fibre paper GF/DVA (Whatman Paper Ltd., England), using a template of the appropriate shape. Paper was cut with the fast wicking side uppermost, and the grain of the paper running across the width of the tracks. Waste material was removed from the slots, switch contacts chamfered, and the position of the fold marked.

Acetate film (0.1 mm thick) was cut to the appropriate size and lightly sprayed on both sides with super 77 spray adhesive (3M USA). This was attached to the slow wicking surface of the proximal portion of main channel, using a pencil mark as a guide, and the protecting channel then bent over to meet the acetate, with about 11 mm between the ends. Surplus acetate was removed flush with the proximal end, leaving 2 mm protruding at the sides.

The channel to be switched, the switch channel, was fixed to this by masking off the last 8 mm on the slow wicking surface, at the contact end, and spraying the exposed area lightly with adhesive. A 0.5 mm thick switch separator (Darvic sheet, ICI, England) was fixed onto the switch channel, and the main and switch channels assembled by gently pressing together.

The expansible switching element was prepared by compressing a 2 mm thick sheet of PVA sponge (average pore size 60 um). Compressed pieces measuring 14 mm by 5 mm were cut out using a scapel. Adhesive was sprayed onto the switching element in a striped pattern, by means of a mask with the stripes running across the width of the switch and the switch then attached to the device with gentle pressure.

Prior to use, when employing reagents immobilised onto Sepharose, small sections of paper were removed from the surface of the device respectively to form grooves defining test and procedural control sites.

In reagent preparation, CNBr activated Sepharose 4B (Pharmacia, Sweden) was washed with 1 mmol/L HCl (200 mL/g Sepharose). Polyclonal anti-HCG antibody (DaKopatts, Denmark), raised in rabbits, was mixed for 2 hours at room temperature with washed Sepharose (1 g Sepharose per 10 mg protein) in 0.1 mol/L carbonate buffer pH 8.3, containing 0.5 mol/L NaCl, (5 mL buffer/g Sepharose). Antibody coated Sepharose was washed with 0.1 mol/L carbonate buffer pH 8.3, containing 0.5 mol/L NaCl. The Sepharose was then blocked by mixing with 0.1 mol/L Tris buffer pH 8.0 for 2 hours. Antibody coated Sepharose was then separated and washed alternately three times with 0.1 mol/L acetate buffer pH 4.0 containing 0.5 mol/L NaCl, and then 1.0 mol/L Tris buffer pH 8.0 containing 0.5 mol/L NaCl. Antibody coated Sepharose particles were finally washed with, and stored in, phosphate buffered saline at 4° C. HCG coated Sepharose was prepared similarly with HCG (Sigma, USA) replacing the anti-HCG antibody.

Also, latex particles, 3 $\mu$m diameter (Sigma, USA), were coated overnight with mouse monoclonal anti-HCG antibody (Quantum Biosystems, England). After washing, the latex was blocked using buffer containing protein and detergent to minimise non-specific binding, and stored at 4° C.

In incorporation of reagents, anti-HCG coated Sepharose, and HCG coated Sepharose were pipetted into the proximal and distal grooves at the test and control sites respectively. 100 $\mu$l of 0.01 mol/l Tris buffer pH 7.6 containing 0.15 mol/L NaCl, 0.1% fish gelatin (Sigma USA), and 1% sucrose was added to each groove, covering the Sepharose and the paper surrounding this area. 50 $\mu$L of a 1:50 dilution of anti-HCG conjugated to horseradish peroxidase (Dakopatts, Denmark), in phosphate buffered saline pH 7.4, was added to each channel approximately 10 mm proximally of the immobilised anti-HCG as the 'first reagent'. 50 $\mu$L of chloronaphthol (0.6 mg/mL in 0.05 mol/L Tris buffer pH 7.5 containing 0.2 mol/L NaCl and 0.02% hydrogen peroxide) was then added to each switch channel as the 'second regent'.

Sample addition involved 50 $\mu$L of HCG standard (0, 250 IU/ml, or dilutions) in PBS containing 0.1% BSA, or a urine specimen, at the immobilised anti-HCG test site. The device was then placed in a close fitting plastic holder, and placed in a 100 mL beaker containing 8 mL of PBS pH 7.4 (containing 0.05% Tween 20) or other appropriate buffers.

EXAMPLE 1

A device employing coated Sepharose particles, HRP conjugate, and chloronaphthol/hydrogen peroxide colorimetric substrate was used as described previously, with PBS pH 7.4, containing 0.05% Tween 20 as the running buffer.

EXAMPLE 2

The above procedure was repeated employing an alkaline phosphatase anti-HCG conjugate. The Sepharose and surrounding paper were blocked using buffer (containing components including protein and detergent) to reduce non-specific binding of reagents. HRP-conjugate was replaced with 50 $\mu$L of a 1 to 100 dilution of anti-HCG alkaline phosphatase conjugate (prepared from a mouse monoclonal antibody, Quantum Biosystems, England) in a diethanolamine based buffer system, pH 9.5. The chloronaphthol colorimetric reagent was replaced by nitrobluetetrazolium (NBT) (Sigma) and 5-Bromo-4-chloro-3-indolyl phosphate (Sigma). HCG standards were added to the reaction site and the device ran using a diethanolamine based buffer, pH 9.5.

EXAMPLE 3

Example 2 was repeated using anti-HCG alkaline phosphatase conjugate and colorimetric substrate from a Tandem Icon II HCG urine assay kit (Hybritech, USA).

EXAMPLE 4

Examples 2 and 3 were repeated with Sepharose replaced by anti-HCG antibody immobilised onto latex particles. The test site was pre-blocked with appropriate buffer, dried, and 25 $\mu$L of antibody coated latex applied and dried onto the site.

In operation, addition of sample starts the reaction between HCG and antibody immobilised onto the paper via the Sepharose particles. Introduction of the base of the device into buffer starts liquid flow up the two channels simultaneously. In the switch channel buffer flow reconstitutes the colorimetric substrate, carrying it to, and concentrating it at, the tip of the channel. As this channel is not initially connected to the main track of the device, further movement of this reagent is prevented. Simultaneously, buffer flow in the main channel proceeds towards the active site, on its way reconstituting and carrying the anti-HCG enzyme labelled conjugate. Buffer flow over the test site removes unbound sample constituents, and delivers conjugate which binds specifically to any immobilised HCG from the sample. Further flow towards the end of the main channel both delivers excess conjugate over the immobilised procedural control (where it binds to the Sepharose bound HCG) and provides a wash step for both the test and procedural control sites. Buffer flow proceeds towards the switch element and, as the front reaches it, buffer passes from the paper into the element. This causes expansion of the element, which presses against the rigid plastic holder and forces the main channel and the switching channel, containing colorimetric substrate, into contact. Once the two channels are in contact, buffer flow is re-established in the switch channel allowing colorimetric substrate to move across to the main channel and towards immobilised enzyme labelled conjugate at the test and control sites. Immobilised enzyme conjugate at these sites acts on substrate to form an insoluble coloured product. Further buffer flow removes substrate from these sites and provides a wash step. Once the buffer reaches the end of the main channel the flow terminates.

Production of coloured product at the test site indicates the presence of HCG (a positive sample), and the depth of colour corresponds to its concentration. High concentrations produce intense colour. A clear unchanged test site is produced if no HCG is present. These responses were observed in all examples (1 to 4). Coloured product at the procedural control site (if present, as in Examples 1 to 3) was produced with positive or negative samples indicating the assays to have been performed correctly with active reagents.

Figure 43:
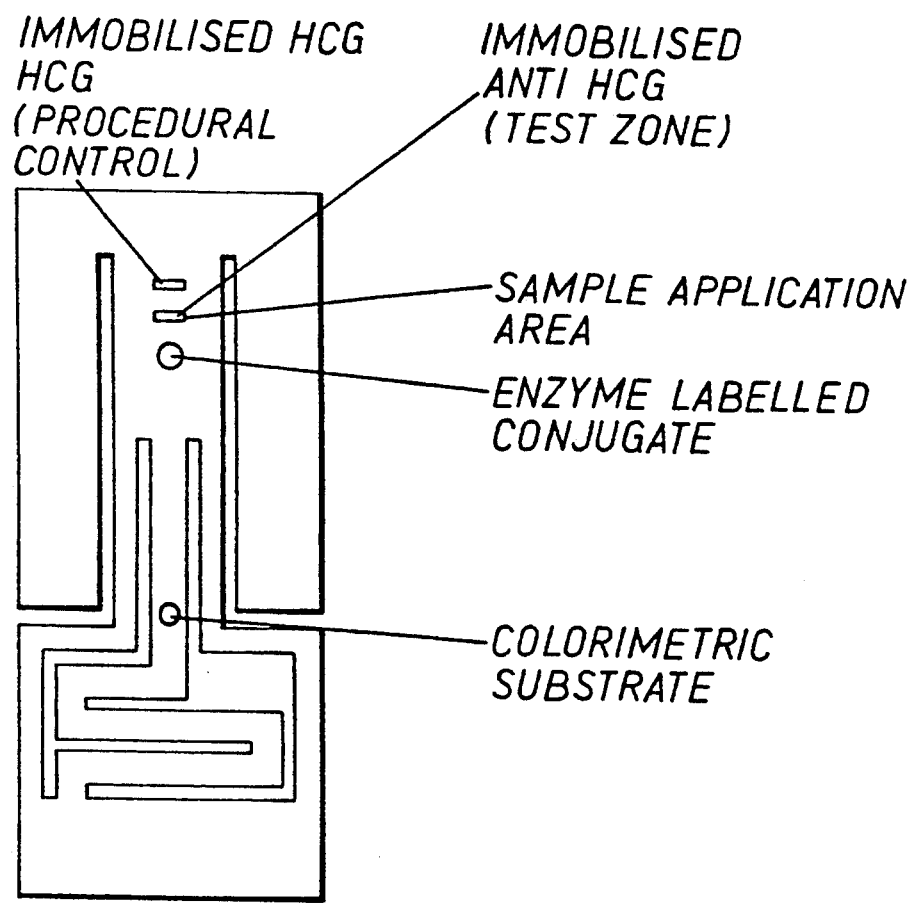
Figure 44:
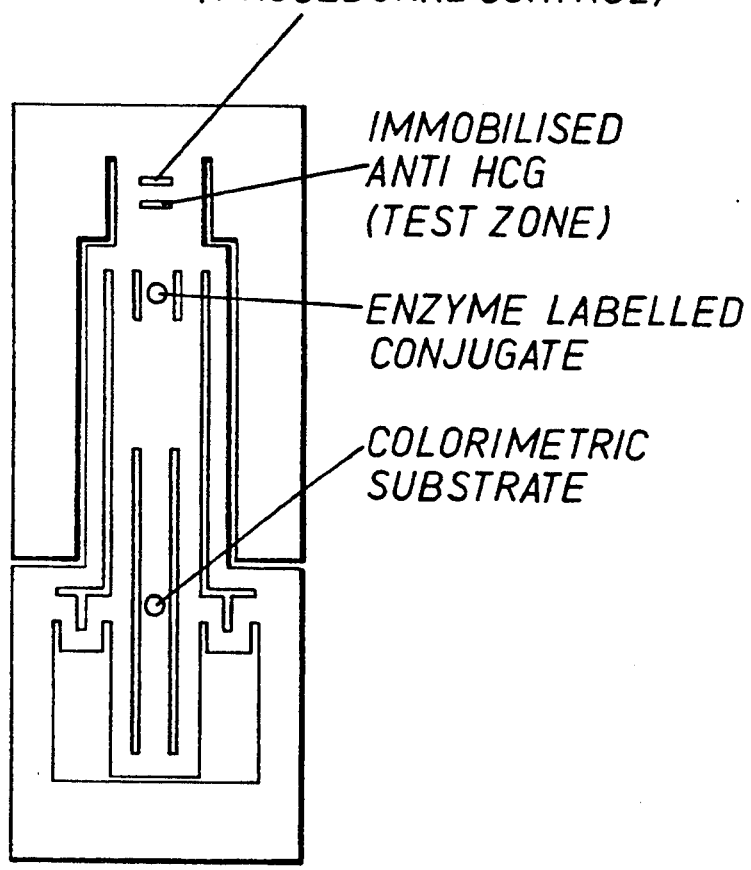
Figure 45:
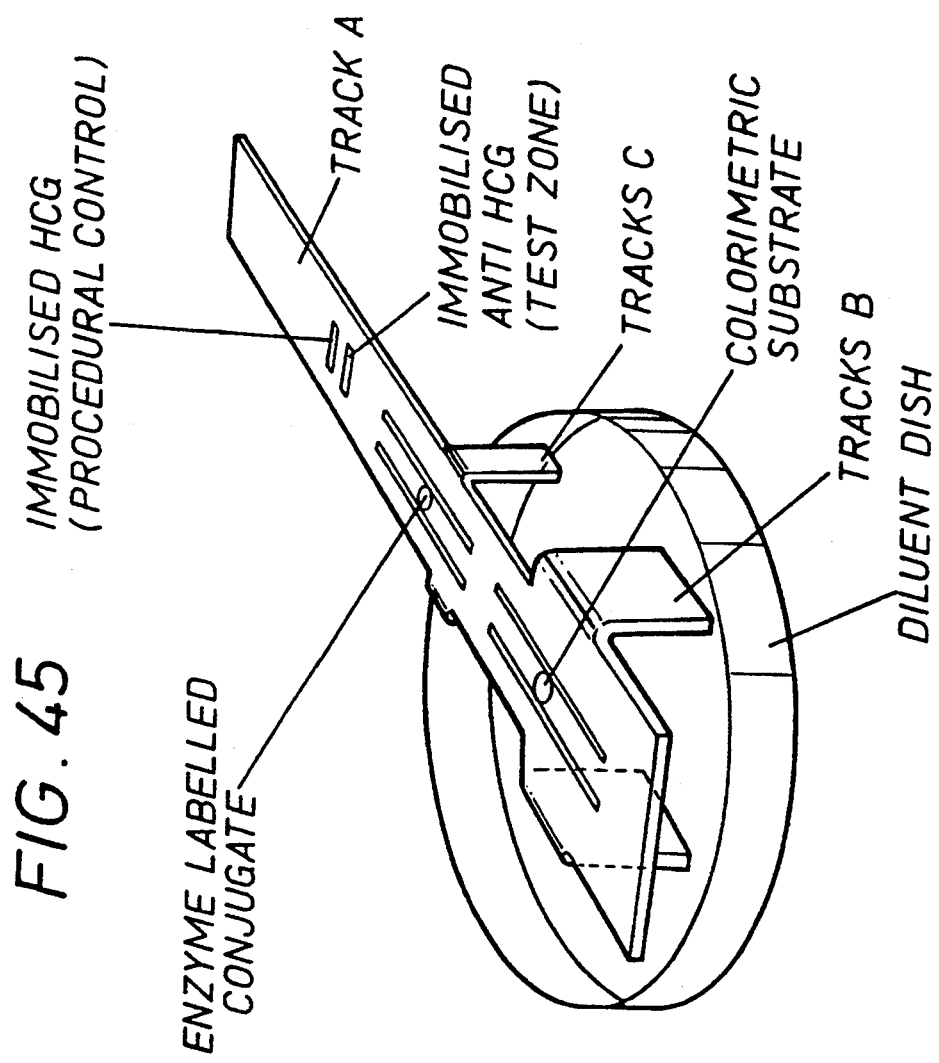

The single layer, or effectively planar, devices of FIGS. 43-45 were cut from sheets of Whatman GF/DVA glass fibre paper (Whatman Paper Ltd. England) using metal templates of the appropriate shape. For FIG. 45 the four side channels used to supply diluent, were bent down at right angles to the main channel.

Sepharose or latex coated particles were positioned on the paper surface at the test or procedural control sites. Small grooves were cut into the surfaces of the paper track at the position of these sites prior to addition of coated Sepharose particles.

In preparation of reagents CNBr activated Sepharose 4B (Pharmacia, Sweden) was washed with 1 mmol/L HCl (200 mL/g Sepharose). Polyclonal anti-HCG antibody (DaKopatts, Denmark) raised in rabbits, was mixed for 2 hours at room temperature with washed Sepharose (1 g Sepharose per 10 mg protein) in 0.1 mol/L carbonate buffer pH 8.3, containing 0.5 mol/L NaCl, (5 ml buffer/g Sepharose). Antibody coated Sepharose was washed with 0.1 mol/L carbonate buffer pH 8.3 containing 0.5 mol/L NaCl. The Sepharose was then blocked by mixing with 0.1 mol/L Tris buffer pH 8.0 for 2 hours. Antibody coated Sepharose was then separated and washed three times alternately with 0.1 mol/L acetate buffer pH 4.0, containing 0.5 mol/L NaCl, and then 1.0 mol/L Tris buffer pH 8.0 containing 0.5 mol/L NaCl. Antibody coated Sepharose particles were finally washed with and stored in phosphate buffered saline at 4° C. HCG coated Sepharose was prepared similarly with HCG (Sigma, USA) replacing the anti-HCG antibody.

Also, latex particles, 3 μm diameter (Sigma, USA) were coated overnight with mouse monoclonal anti-HCG antibody (Quantum Biosystems, England). After washing, the latex was blocked using buffer containing protein and detergent, and stored at 4° C.

In incorporation of reagents, anti-HCG and HCG coated Sepharose was pipetted into the proximal and distal grooves respectively of the device of FIG. 43. 200 μl of 0.01 mol/l Tris buffer pH 7.6, containing 0.15 mol/L NaCl, 0.1% fish gelatin (Sigma USA), and 1% sucrose was added to cover the Sepharose and the paper surrounding this area. Anti-HCG conjugated to horseradish peroxidase (DaKopatts, Denmark) 100 μl of a 1:50 dilution of conjugate in phosphate buffered saline pH 7.4, was incorporated onto the device proximally of the test sites. 100 μL of chloronaphthol (0.6 mg/mL in 0.05 mol/L Tris buffer pH 7.5 containing 0.2 mol/L NaCl and 0.02% hydrogen peroxide) was added to the central channel of FIG. 43.

Devices of FIGS. 43-45 were also prepared similarly using Sepharose coated particles. 50 μL of alkaline phosphatase conjugate and 50 uL alkaline phosphatase colorimetric substrate (Hybritech, USA) were incorporated where shown (FIGS. 44 and 45).

Sample addition involved 50 μL of HCG standard (0, 250 IU/mL or dilutions in PBS containing 0.1% BSA), or a patient's urine sample, at the immobilised anti-HCG test site, followed by immersion of the proximal base (FIGS. 43 and 44) or bent side channels (FIG. 45) into the buffer.

EXAMPLE 1

Device 1 prepared using coated Sepharose, horseradish peroxidase conjugate and chloronaphthol/hydrogen peroxide colorimetric substrate was operated using PBS buffer pH 7.4, containing 0.05% Tween 20 as the running buffer.

EXAMPLE 2

The above procedure was repeated, employing an alkaline phosphatase anti-HCG conjugate, with each of the devices. The Sepharose and surrounding paper track were blocked using buffer containing components including protein and detergent to reduce non-specific binding of reagents. The HRP-conjugate was replaced with anti-HCG alkaline phosphate from an Icon II HCG kit (Hybritech, USA). Chloronaphthol colorimetric reagent was replaced by alkaline phosphate colorimetric reagent from a Hybritech Icon II HCG kit. HCG standards were added to the test site and the devices operated using a diethanolamine based buffer, pH 9.5.

EXAMPLE 3

Example 2 was repeated with Sepharose replaced by anti-HCG antibody immobilised onto latex particles. The test site was preblocked with appropriate buffer, dried and 25 μL of antibody coated latex applied an dried onto the site.

In operation of FIG. 43, sample addition starts the reaction between HCG and antibody immobilised onto the paper via the Sepharose particles. Introduction of the base of the device into buffer starts liquid flow up the paper.

Buffer travels up toward the reservoirs at the top of the device along the two side channels and the longer central channel. Buffer moves from the two side channels and then up the central common channel towards the test site. As it does so, it reconstitutes and carries enzyme labelled antibody with it. Flow over the site removes any unbound sample constituents and allows enzyme labelled conjugate to react with any immobilised HCG. Further flow produces a wash step and passes excess conjugate over the procedural control site where it reacts with the HCG coated Sepharose.

Simultaneously, some buffer from the side channels flows down towards that travelling directly up the central track. These fronts converge and reconstitute the colorimetric substrate. Convergence of the initially opposed flow fronts concentrates the reconstituted substrate. Once the fronts have converged, this portion of the channel is saturated, and flow only occurs up the central channel. This produces further washing of the test and control sites and delivers colorimetric substrate to these sites. Immobilised enzyme conjugate at these positions acts on substrate to from a coloured product. Further buffer flow removes substrate from sites and provides a wash step. Once the buffer reaches the end of the two reservoirs, flow terminates.

The device of FIG. 44 operates similarly, but the geometry is such that a longer buffer wash through the test site is produced, prior to delivery of the conjugate. Also, the reconstituted enzyme labelled antibody is concentrated by the provision of slots alongside the relevant site, whereby the site is narrowed and opposed flows converge.

The device of FIG. 45 also operates in similar manner. However, connection of the side channels directly to the buffer supply allows reconstitution of the separate reagents with minimal delay, and more rapid subsequent sequential washes and delivery of reagents to the test and contact sites.

Devices such as those of FIGS. 44 and 45, respectively, can in fact be folded back along each of their central pairs of slots and arranged in a multiple assembly with successive devices separated by a layer of impervious material and their central areas coplanar.

It will already be appreciated that the invention is open to considerable variation in device form. Similarly the invention is open to variation in the form of assay which it can be used to implement.

We claim:

1. A liquid transfer device for use in assay procedures, comprising:
    a first, second and third liquid flow channel each having a first and second end and being of porous material for liquid flow therethrough by capillary action from the first to the second end;
    respective connections being provided between the second ends of said first and second channels and the first end of said third channel to deliver liquid flow from the former to the latter as a common channel;
    said first and second channels having mutually different structural forms to cause respective simultaneously-initiated liquid flows therethrough to arrive at said third channel first end one after the other; and
    the connection to said third channel first end of said second end of at least said one flow channel defining a liquid delivery flow path therebetween which is substantially symmetrically disposed across the width of said third channel.

2. A device according to claim 1, wherein said one flow channel second end is connected with said third channel first end over only a central transversely disposed portion of the latter.

3. A device according to claim 1, wherein said one flow channel includes two structurally like subsidiary channels having respective second ends connected in mutually spaced manner with said third channel first end.

4. A device according to claim 1, wherein said first channel second end is connected with said third channel first end over only a central transversely disposed portion of the latter; and
    said second channel includes two structurally like subsidiary channels disposed on respective opposite sides of said first channel, and having respective second ends connected with said third channel first end in symmetrical manner about said first channel second end.

5. A device according to claim 1, wherein said first, second and third channels are provided as interconnected parts of a single sheet of said porous material.

6. A device according to claim 5, wherein said first sheet is substantially planar.

7. A device according to claim 5, wherein said channels are individually defined by an absence of said material.

8. A device according to claim 5, wherein said channels are individually defined by application of an agent to render said material between them impervious to liquid.

9. A device according to claim 1, wherein said first and second channels contain respectively different analytical reagents to be carried to said third channel by said liquid flows.

10. A liquid transfer device for use in assay procedures, comprising:
    a first and second liquid flow channel leading from a respective pair of channel ends to a common site;
    said channels and site being formed, at least in part, of respectively different portions of a single sheet of porous material for liquid flow therethrough by capillary action;
    said channels having mutually different structural forms to cause respective simultaneously-initiated liquid flows therethrough to arrive at said site one after the other; and
    at least one of said channels including two structurally like subsidiary channels leading to said site in mutually-spaced symmetrical manner.

11. A device according to claim 10, wherein said sheet is substantially planar.

12. A device according to claim 10, wherein said channels contain respectively different analytical reagents to be carried to said site by said liquid flows.

* * * * *